Jan. 4, 1927. Re. 16,521

L. ZACHARA

ELECTRIC SPECTACLE

Original Filed March 12, 1920

Inventor

Ladislaus Zachara

Reissued Jan. 4, 1927.

Re. 16,521

UNITED STATES PATENT OFFICE.

LADISLAUS ZACHARA, OF BREMERTON, WASHINGTON.

ELECTRIC SPECTACLE.

Original No. 1,488,085, dated March 25, 1924, Serial No. 365,200½, filed March 12, 1920. Application for reissue filed August 21, 1924. Serial No. 733,452.

The present invention relates to illuminating devices and more particularly to illuminating devices adapted to directly illuminate the path of vision. A feature of the invention is the provision of a spectacle or goggle in combination with the illuminating device to protect the eyes.

Devices of this character are especially useful to motorists, garage men and others who desire a portable light which may be attached to the user in such manner as to give complete freedom of the hands and arms.

An object of the invention is the provision of an illuminating device that occupies a small amount of space and can be folded to a convenient shape to adapt the same to fit into a case, the pocket of the user, or the door of an automobile.

Another object of the invention is the provision of improved connections for supplying current to the illuminating element of such a device.

A still further object of the invention is the provision of a multiple pole switch for controlling the illuminating elements when several are employed.

A still further object of the invention is the provision of an illuminating element composed of two separate lighting members to permit a greater range of light control.

Still another object of the invention is the provision of a carrying case for the device whereby the same may be converted into a lantern.

That the invention may be better understood, reference is had to the drawings wherein.

Figure 12:
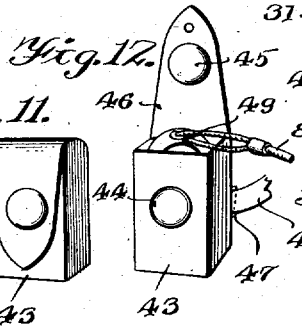
Figure 11:
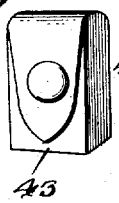
Figure 10:
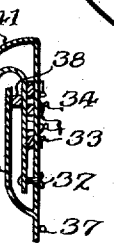
Fig. 10 is a sectional view of the multiple pole switch shown diagrammatically in Fig. 9.
Figure 14:
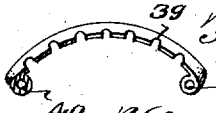
Figure 13:
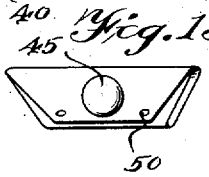

Fig. 11 discloses a front elevation of a carrying case, in its closed position;

Fig. 12 discloses a front elevation of a carrying case in its open position showing the arrangement of the lead wire;

Fig. 13 shows a modified form of carrying case;

Fig. 14 shows a slotted bar which may be used to retain the multiple pole switch in fixed position.

A goggle or spectacle frame is designated by the numeral 1 and is preferably made from sheets of flexible covering material attached to a flexible frame to permit folding of the device. Mounted on the outer face of the nose portion of the goggle is a socket member 2 which is adapted to receive a miniature lamp 53. An annular lamp 51 surrounds the lamp 53.

The mounting of the illuminating element on the nose portion of the device has the special advantage that the eyes may be shielded from any glare by surrounding the element with a reflecting surface. If the illuminating element is mounted elsewhere difficulty is encountered in this respect. Furthermore this positioning of the illuminating element insures light directly in the path of vision.

Figure 1:
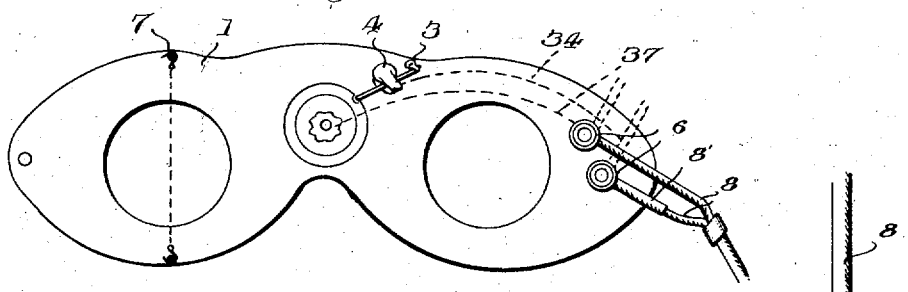
Fig. 1 is a front view of the device showing a goggle frame member, and an illuminating element mounted on the nose portion thereof.

The illuminating element is controlled by a switch which comprises a bar 3, pivotally mounted to the goggle by the rivet 5, as shown in Fig. 1, and a clip 4 which is adapted to receive and retain the bar member 3. The switch is connected in the circuit by fastening one end of a lead wire to the clip 4 and connecting the arm 3 directly to the socket or by means of a wire to one of the socket contact members.

The wiring 34 and 37 is connected with a source of current through means of the binding posts 6, the latter being attached to current supply wires 8. To protect the ends of the current supply wires 8 and guard against their breaking, they are covered with a sleeve 8′ which may be constructed from rubber tubing or the like. The sleeve gives added rigidity to the wire and prohibits sharp bending and twisting.

Figure 2:
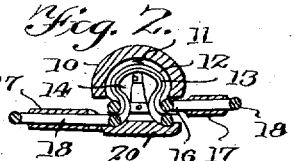
Fig. 2 is a cross sectional detailed view of one type of contact member.
Figure 3:
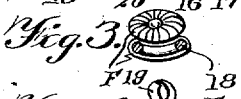
Fig. 3 is a detailed view of the female portion of a modified form of contact member, showing an annular groove provided for reception of the lead wires.
Figure 4:
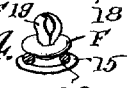
Fig. 4 is a detailed view of the male portion of a modified form of the contact member, showing an annular groove, provided for reception of the lead wires.

The binding posts 6 are constructed as shown in Figs. 2, 3 and 4. This construction comprises, a female member, shown in Fig. 2, which includes a hollow spherically shaped cap portion 10, which is preferably made from insulating material, a lining member 12 which is formed to interfit with the interior of said cap portion and which is curved outwardly at the edge. A second lining member 13 is secured in adjacent relationship to the lining member 12 and is curved at the edge to form an annular groove with the edge of the lining member 12. The said groove is adapted to receive a current supply wire 18. The male contact member is normally of spherical shape and is composed of a plurality of resilient leaves 19 which are adapted to pass through the base portion of the female contact and interfit therewith. A spring 11 is interposed between the top of the female lining member 12 and the cap 10 to force the former down against the male contact. An insulated base member 20 is secured to the male portion of the contact member. The lead wire 18 is connected by means of an annular groove or flange F provided at the base of the male contact member.

Figure 5:
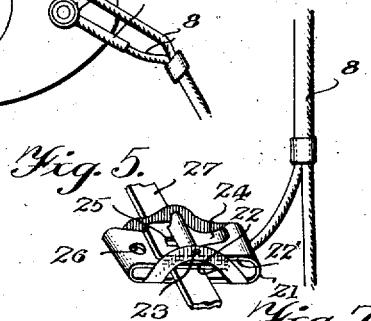
Fig. 5 is a view of a clamping member which is adapted to fit upon and make electrical connection with the contact blade of a flashlight battery.
Figure 6:
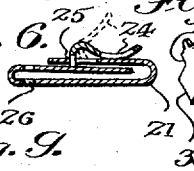
Fig. 6 is a sectional view of the clamping member shown in Fig. 5.
Figure 7:
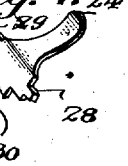
Fig. 7 is a detailed view of a lever used to compress the clamping member shown in Figs. 5 and 6.

A clamping member for making connections to the ordinary dry battery having a flat spring contact blade is shown in Fig. 5. The body portion of the clamping member is composed of a single piece of metal so fashioned as to provide side arch members 22 which are adapted to receive a locking lever 24. The ends 21 and 22′ of the body portion are bent inwardly so that they overlap each other with the end 22′ on top. The end 22′ is provided with a transverse slot 25 which is adapted to receive the projection 30 provided on the lever 24. The arch members 22 are provided with aligned openings 23 to receive the trunnions 28 of the lever 24. Provision is made for connecting a lead wire to the clamping member by drilling through the same at the point 26 and soldering the wire in place.

The clamp is slipped over the battery contact 27, as shown in Fig. 5, and the lever 24 is depressed to make a snug contact between the center and bottom portions of the clamp with the battery contact blade. Upon lifting the lever the clamp is released.

Figure 8:
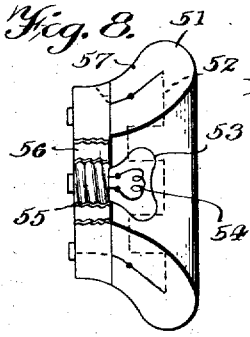
Fig. 8 is a sectional view of an illuminating element composed of an annular lamp with a minature lamp mounted in the center thereof.

An illuminating element is shown in Fig. 8. This comprises an annular lamp 51 which is provided with a filament 52, a bushing 56 which is interposed between the annular lamp and a miniature lamp socket 55. A miniature lamp 53 is provided with a filament 54 and is mounted in the socket 53. The outer wall 57 of the annular lamp may be mirrored to form a reflector and if desirable, the mirroring may be colored.

Figure 9:
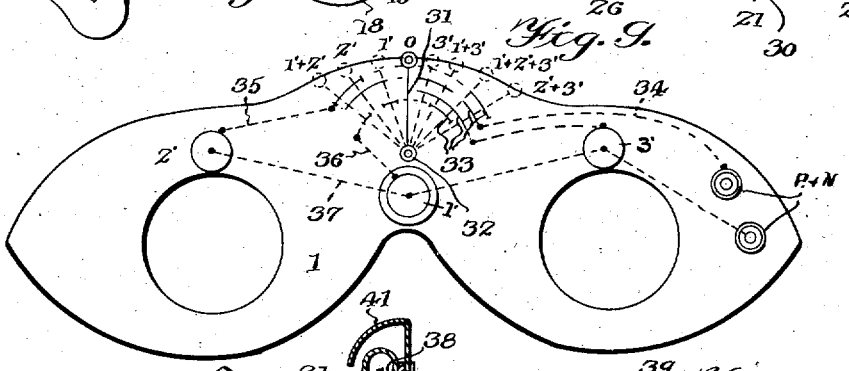
Fig. 9 is a view of the device showing a plurality of lamp sockets and the arrangement of a switch for distributing the current to the same either individually or in any desired combination.

A modified form of the invention is shown in Fig. 9. This embodiment of the invention includes not only the central illuminating element but also several other lighting elements 21 and 31. These members are controlled by a multiple pole switch (shown diagrammatically) which enables the wearer to light any single light or combination of lights, as indicated by the numerals in the drawing. The wiring for this switch is indicated by the numerals 35, 35′, 36 and 37.

The switch is composed of a back portion and a hood portion 41 which is integral with the back portion and bent over the top of the switch to protect the same. The contacts 33 are mounted on the back portion and radiate from the center of the switch. They are placed in circuit by means of the switch arm 31 which is pivotally mounted at the central point 32. Suitable insulation is provided to prevent grounding of the various members to the back. The bottom portion of the switch is enclosed by a shield 42 which extends from the base of the back upward over the terminals to a point approximately opposite the end of the hood 41. The switch arm 31 is bent in the shape of a U so as to extend over the edge of the shield 42 and below the hood 41.

To fix the switch lever at any particular group of terminals a stop bar 38, shown in Fig. 4, is provided. This stop bar is interposed between the back member and the switch arm and is equipped with a plurality of slots or recesses 39 which are adapted to receive the switch arm 31 and retain the same in fixed position.

A carrying case is shown in Figs. 12 and 13. This case is prism-shaped and adapts the goggle for use as a lantern or torch. An opening 44 is provided in the wall 43, which is oppositely disposed to the illuminating element when the goggle 49 is folded and placed within the case. The top 46 is equipped with an opening 45 which superimposes the opening 44 when the cover is folded over and fastened in the closed position. A catch member 47 is positioned on the back of the case and is adapted to receive a man's belt or other support so that the case may be fastened to the wearer.

A modified form of the case is shown in Fig. 13. This embodiment of the invention is shaped like an envelope and is adapted to carry the spectacle flattened out. The flap and front wall of the case are provided with suitable openings oppositely disposed to the illuminating element when the spectacle is within the case. A fastening member 50 is provided to retain the flap in place.

The device is compact and can be supplied with current from an ordinary flashlight battery which may be conveniently carried in the pocket of the user.

I claim:

1. An electric spectacle, comprising a frame, an illuminating element mounted on said frame, said illuminating element being composed of two electric lamps, one being mounted within the other, the outer lamp being formed to constitute a reflector for the inner lamp and having a wall thereof coated with a reflecting medium.

2. A spectacle comprising a frame, a plurality of lamps mounted on said frame, a multiple pole switch, wiring connecting said switch and said lamps, said switch comprising a casing having a rear wall, a front wall spaced therefrom and joining the rear wall at its lower edge, a switch arm pivotally connected to said casing and extending from the interior thereof over the outer side of said front wall, a stop bar positioned within said casing, said stop bar being adapted to retain said switch arm in any desired position, contact members suitably positioned within said casing, and a hood extending from the rear wall of the said casing over and above the said switch arm.

3. An electric spectacle comprising a frame, an illuminating element mounted on the nose portion of said frame, and contact members, said contact members comprising male and female portions, said female portion having an outer wall, a spherical lining within said wall, a spring interposed between said outer wall and said lining, said male portion having a base, resilient leaves associated therewith and adapted to interfit with the lining of said female portion.

4. An electric spectacle, comprising a frame, an illuminating element positioned on said frame, a feed cord for supplying electricity to said illuminating element, contact clamps attached to one end of said feed cord, said clamps comprising a body portion formed from a single piece of conductive material into three spaced layers, the topmost layer being slotted to receive a compressing lever, the lowermost layer having arch members integral therewith and bent at right angles thereto, a lever associated with said arch members and passing through the slot in the said top layer, said lever being adapted to compress the second layer toward the lowermost layer.

5. The combination with an electric spectacle provided with an illuminating element, of a case, said case having an opening in its front wall, lens carried by the covering portion, said lens aligning with the said opening and illuminating element when the covering portion is closed to permit light to be projected therethrough.

6. An electric spectacle comprising a flexible frame and an illuminating element mounted on the nose portion of said frame, said illuminating element comprising a central electric lamp, an annular lamp surrounding the central lamp, a source of electric current, and wiring connecting the illuminating element with said source of current.

7. An electric spectacle comprising a flexible curved goggle frame, a pliable covering for said frame having openings therein to receive lens, said frame and said covering being so shaped and flexible to the degree that it will conform to substantially the features of a wearer, a socket member adapted to receive an electric lamp mounted on the nose portion of said covering, a reflecting member surrounding said socket member, said socket member and reflecting member being so mounted in relation to the openings provided in said covering that light emanating from a lamp in said socket member will be directed in the path of vision, and means associated with said socket and said flexible covering to electrically connect said socket to a source of current.

In testimony whereof I have hereunto subscribed my name.

LADISLAUS ZACHARA.